United States Patent
Brownhill

(10) Patent No.: US 9,901,452 B2
(45) Date of Patent: Feb. 27, 2018

(54) RADIAL HEAD IMPLANT

(71) Applicants: MAYO FOUNDATION FOR MEDICAL EDUCATION AND RESEARCH, Rochester, MN (US); IMDS Corporation, Logan, UT (US)

(72) Inventor: James Brownhill, Orlando, FL (US)

(73) Assignees: IMDS Corporation, Providence, UT (US); Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 13/827,985

(22) Filed: Mar. 14, 2013

(65) Prior Publication Data

US 2014/0277524 A1  Sep. 18, 2014

(51) Int. Cl.
*A61F 2/38* (2006.01)
*A61F 2/30* (2006.01)

(52) U.S. Cl.
CPC .... *A61F 2/3804* (2013.01); *A61F 2002/3013* (2013.01); *A61F 2002/30112* (2013.01); *A61F 2002/30136* (2013.01); *A61F 2002/30332* (2013.01); *A61F 2002/30354* (2013.01); *A61F 2002/30934* (2013.01); *A61F 2002/30935* (2013.01); *A61F 2002/3809* (2013.01); *A61F 2002/3818* (2013.01); *A61F 2002/3827* (2013.01)

(58) Field of Classification Search
CPC ...... A61F 2002/2871; A61F 2002/3827; A61F 2002/3809; A61F 2002/3818
See application file for complete search history.

(56) References Cited

U.S. PATENT DOCUMENTS

| | | | |
|---|---|---|---|
| 4,242,758 A * | 1/1981 | Amis et al. | 623/20.11 |
| 4,383,337 A | 5/1983 | Volz | |
| 5,879,395 A | 3/1999 | Tornier | |
| 5,935,172 A | 8/1999 | Ochoa et al. | |
| 6,217,616 B1 | 4/2001 | Ogilvie | |
| 6,270,529 B1 | 8/2001 | Terrill Grisoni | |
| 6,361,563 B2 | 3/2002 | Terrill Grisoni | |
| 6,656,225 B2 | 12/2003 | Martin | |

(Continued)

FOREIGN PATENT DOCUMENTS

| | | |
|---|---|---|
| EP | 624352 | 10/1997 |
| EP | 1080701 | 8/2006 |

(Continued)

OTHER PUBLICATIONS

Wikipedia.org—pear (fruit)—obtained on Dec. 11, 2015.*

(Continued)

*Primary Examiner* — David H Willse
(74) *Attorney, Agent, or Firm* — Schwegman Lundberg & Woessner, P.A.

(57) ABSTRACT

A radial head prosthesis for implantation in a distal radius. The implant includes a head portion and a stem portion. The stem portion has a cylindrical shaft and tapered tip. The head portion includes a recess for engagement with the stem portion. The head portion includes a first bearing surface for articulation with a humerus, and a second bearing surface for articulation with an ulna. The second bearing surface includes at least one concave and one convex portion immediately adjacent one another.

16 Claims, 9 Drawing Sheets

(56) References Cited

U.S. PATENT DOCUMENTS

| | | |
|---|---|---|
| 6,709,459 B1 | 3/2004 | Cooney |
| 6,767,368 B2 | 7/2004 | Tornier |
| 7,160,329 B2 | 1/2007 | Cooney |
| 7,608,110 B2 | 10/2009 | O'Driscoll |
| 7,641,695 B2 | 1/2010 | Guederian |
| 7,708,781 B2 | 5/2010 | Scheker |
| 7,740,661 B2 | 6/2010 | Baratz |
| 8,034,116 B2 | 10/2011 | Vander Meulen |
| 8,048,162 B2 | 11/2011 | Scheker |
| 8,110,005 B2 | 2/2012 | Berelsman |
| 8,114,163 B2 | 2/2012 | Berelsman |
| 8,366,781 B2 | 2/2013 | Berelsman |
| 8,377,066 B2 | 2/2013 | Katrana |
| 2004/0186580 A1 | 9/2004 | Steinmann |
| 2004/0225367 A1* | 11/2004 | Glien .................. A61F 2/3603 623/19.14 |
| 2005/0075735 A1 | 4/2005 | Berelsman et al. |
| 2005/0216090 A1* | 9/2005 | O'Driscoll ............ A61F 2/3804 623/20.32 |
| 2005/0246032 A1* | 11/2005 | Bokros et al. ............... 623/23.6 |
| 2006/0052725 A1 | 3/2006 | Santilli |
| 2008/0288079 A1 | 11/2008 | Leibel |
| 2009/0240336 A1 | 9/2009 | Vander Meulen et al. |
| 2009/0281631 A1 | 11/2009 | Naidu |
| 2010/0030339 A1 | 2/2010 | Berelsman |
| 2010/0121390 A1 | 5/2010 | Kleinman |
| 2010/0241236 A1 | 9/2010 | Katrana |
| 2010/0262252 A1 | 10/2010 | Berelsman |
| 2010/0312349 A1 | 12/2010 | Berelsman |
| 2011/0029089 A1* | 2/2011 | Giuliani .................. A61F 2/40 623/19.14 |
| 2011/0112649 A1 | 5/2011 | Isch |
| 2011/0125276 A1 | 5/2011 | Berelsman |
| 2011/0144759 A1 | 6/2011 | Berelsman |
| 2011/0172781 A1 | 7/2011 | Katrana |
| 2012/0083892 A1 | 4/2012 | Kehres |
| 2012/0109323 A1 | 5/2012 | Berelsman |
| 2014/0012388 A1 | 1/2014 | Brownhill et al. |
| 2014/0074246 A1 | 3/2014 | Huebner |
| 2016/0051365 A1 | 2/2016 | Brownhill et al. |

FOREIGN PATENT DOCUMENTS

| | | | |
|---|---|---|---|
| EP | 1772118 | 6/2009 | |
| EP | 2 078 511 A1 * | 7/2009 | ............... A61F 2/38 |
| EP | 2078511 | 10/2010 | |
| EP | 2 561 833 A1 * | 2/2013 | ............... A61F 2/38 |
| WO | WO-0013617 A1 | 3/2000 | |
| WO | WO-2004000174 A1 | 12/2003 | |
| WO | WO-2005086939 A2 | 9/2005 | |
| WO | WO-2006060322 A1 | 6/2006 | |
| WO | WO2010098791 | 9/2010 | |
| WO | WO2011017620 | 2/2011 | |
| WO | WO-2014159203 A1 | 10/2014 | |
| WO | WO-2014160924 A1 | 10/2014 | |

OTHER PUBLICATIONS

"International Application Serial No. PCT/US2014/022495, International Search Report dated Jun. 25, 2014", 4 pgs.

"International Application Serial No. PCT/US2014/022495, Written Opinion dated Jun. 25, 2014", 6 pgs.

"U.S. Appl. No. 14/779,872, Preliminary Amendment Filed Sep. 24, 2015", 7 pgs.

"Application Serial No. PCT/US2014/032151, International Preliminary Report on Patentability dated Oct. 8, 2015", 8 pgs.

"International Application Serial No. PCT/US2014/022495, International Preliminary Report on Patentability dated Sep. 24, 2015", 8 pgs.

"International Application Serial. No. PCT/US2014/032151, International Search Report dated Jul. 2, 2014", 3 pgs.

"International Application Serial No. PCT/US2014/032151, Written Opinion dated Jul. 2, 2014", 6 pgs.

"European Application Serial No. 14717907.1, Response filed May 16, 2016 to Communication pursuant to Rules 161(1) and 162 EPC dated Nov. 5, 2015", 10 pgs.

"European Application Serial No. 14719503.6, Response filed Jun. 13, 2016 to Communication pursuant to Rules 161(1) and 162 EPC dated Dec. 2, 2015", 11 pgs.

"U.S. Appl. No. 14/779,872, Non Final Office Action dated Feb. 10, 2017", 11 pgs.

"European Application Serial No. 14719503.6, Communication Pursuant to Article 94(3) EPC dated Nov. 29, 2016", 4 pgs.

"European Application Serial No. 14719503.6, Response filed Apr. 11, 2017 to Communication Pursuant to Article 94(3) EPC dated Nov. 29, 2016", 12 pgs.

"Application Serial No. 14/779,872, Response filed May 10, 2017 to Non Final Office Action dated Feb. 10, 2017", 16 pgs.

"U.S. Appl. No. 14/779,872, Final Office Action dated Aug. 29, 2017", 14 pgs.

"U.S. Appl. No. 14/779,872, Response filed Oct. 30, 2017 to Final Office Action dated Aug. 29, 2017", 17 pgs.

* cited by examiner

RADIAL HEAD IMPLANT

CROSS-REFERENCE TO RELATED APPLICATIONS

None.

FIELD OF THE DISCLOSURE

The present disclosure is directed toward implants for joint arthroplasty and methods of implantation. The embodiments disclosed may be used in a radial head replacement procedure.

BACKGROUND OF THE INVENTION

Indications for the replacement of the radial head can include: a) degenerative or post-traumatic disabilities presenting pain, crepitation, and decreased motion at the radio humeral and/or proximal radioulnar joint with: joint destruction and/or subluxation visible on x-ray; and/or resistance to conservative treatment; b) primary replacement after fracture of the radial head; c) symptomatic sequelae after radial head resection; and d) revision following failed radial head arthroplasty.

In radial head replacement procedures, a radial head prosthesis is implanted into the intramedullary canal of the proximal radius. The radial head may cooperate with an ulna or ulnar prosthesis to provide radioulnar joint articulation. The radial head may cooperate with a humerus or humeral prosthesis to provide radiohumeral joint articulation.

Some radial head implants known in the art include a head portion having a cylindrical shape and/or straight sides. These implants may provide only point contact with an ulnar component. In addition, it can be difficult to implant a radial head prosthesis into the intramedullary canal at a precise angle or relationship to the ulna. If the radial implant is not inserted at a precise angle relative to the ulnar component, surface contact with the ulnar or ulnar prosthesis may not be achieved.

Disclosed herein is a radial head implant including a head and a stem. In an embodiment, the head portion is symmetric and non-cylindrical, and has sides formed of multiple arc segments, with no straight sections. This shape provides surface contact between the radial head and an ulna or ulnar component. This shape also accommodates a radius whose proximal canal axis is not parallel with the articulation surface of an ulnar component. A concave portion is provided near a distal end of the head, which may provide easier insertion into the joint space by permitting a smaller angle of approach to the radial medullary canal when passing near the distal humerus. In an embodiment, the stem is straight and has a bullet-shaped tip, which may provide easier insertion into the intramedullary canal than would other shapes including a squared-off end.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
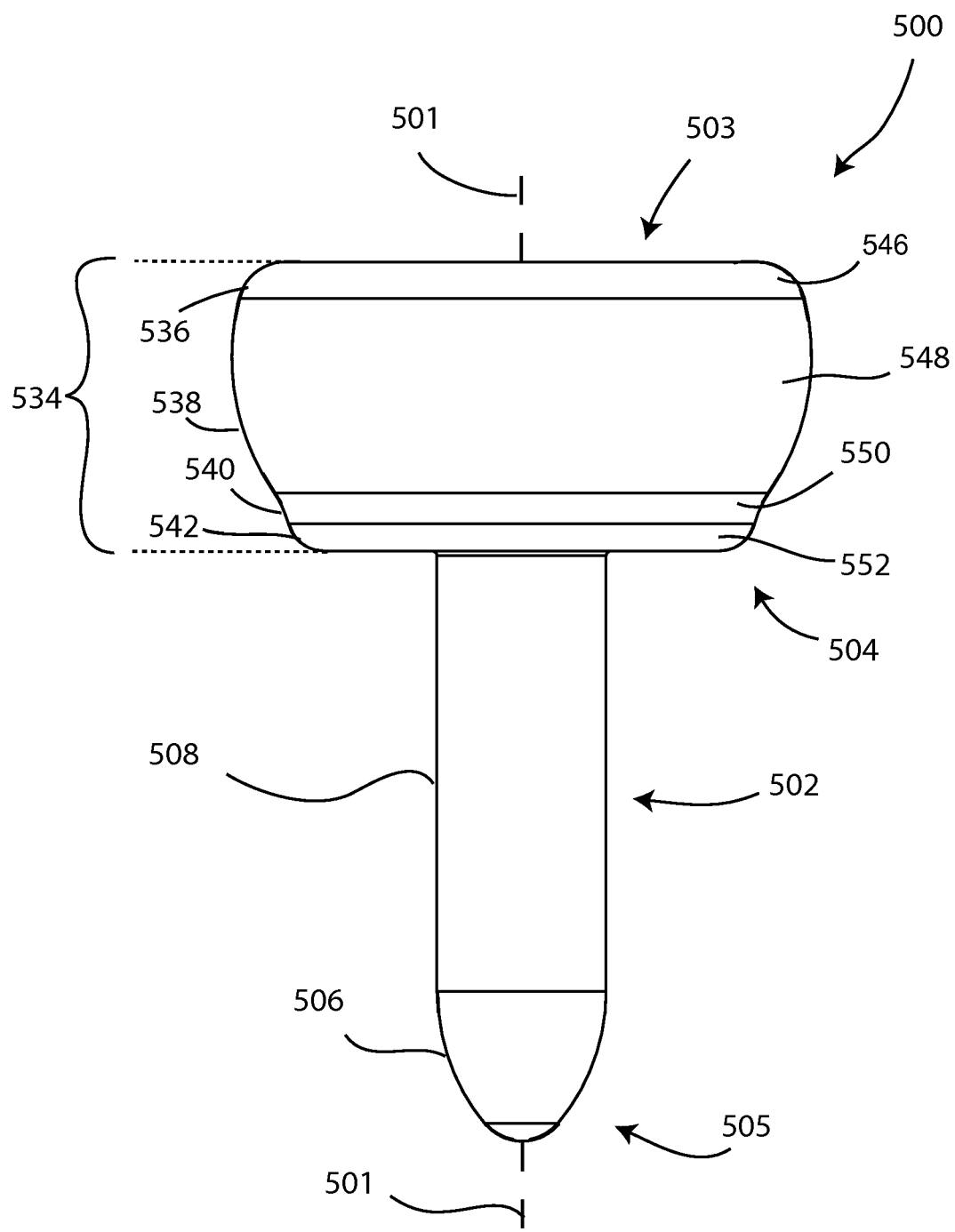
FIG. 1 is a side view of an embodiment of a radial head implant including a stem portion and a head portion.
Figure 2:
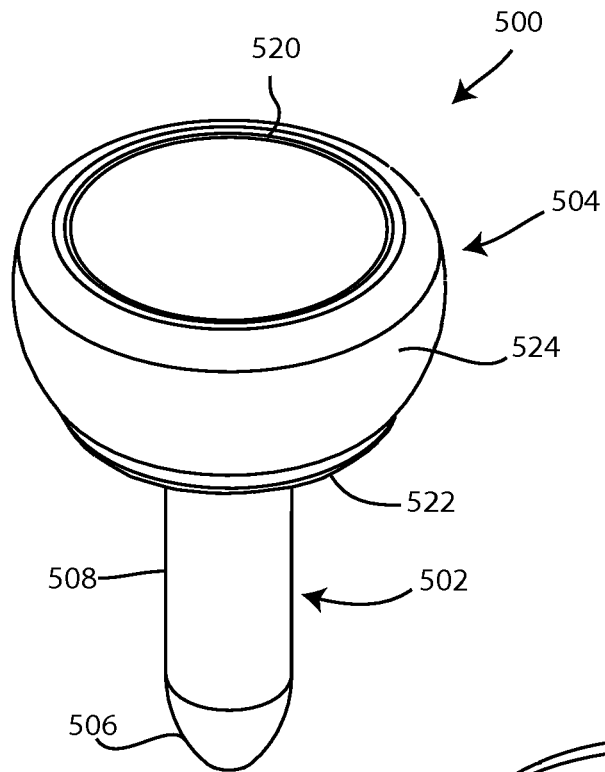
FIG. 2 is a top isometric view of the radial head implant of FIG. 1.
Figure 3:
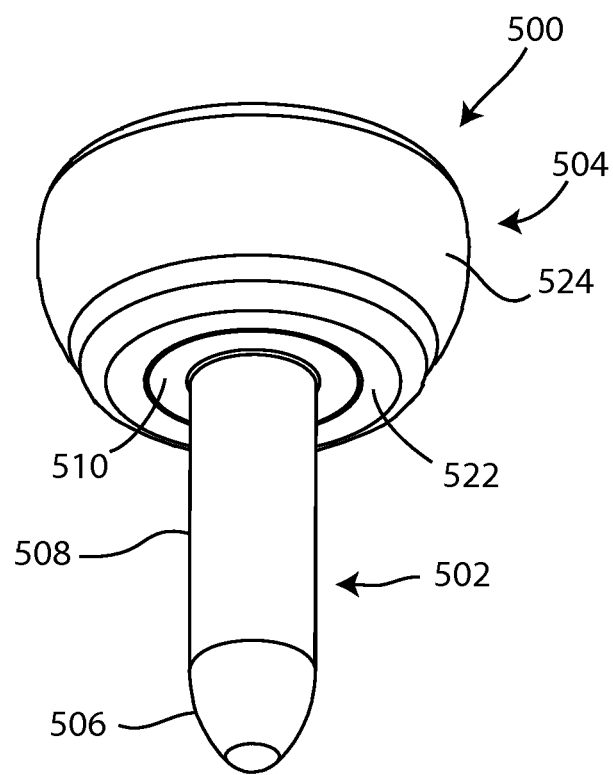
FIG. 3 is a bottom isometric view of the radial head implant of FIG. 1.
Figure 4:
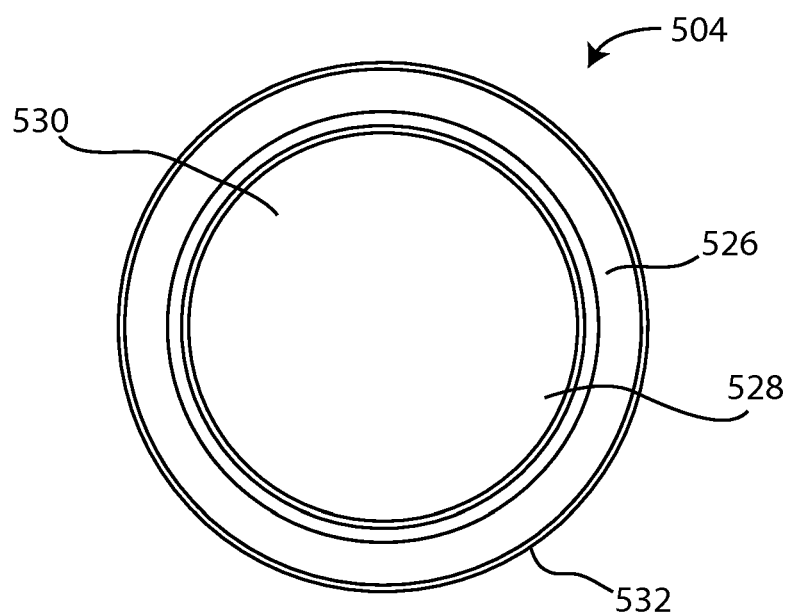
FIG. 4 is a top view of the radial head implant of FIG. 1.
Figure 5:
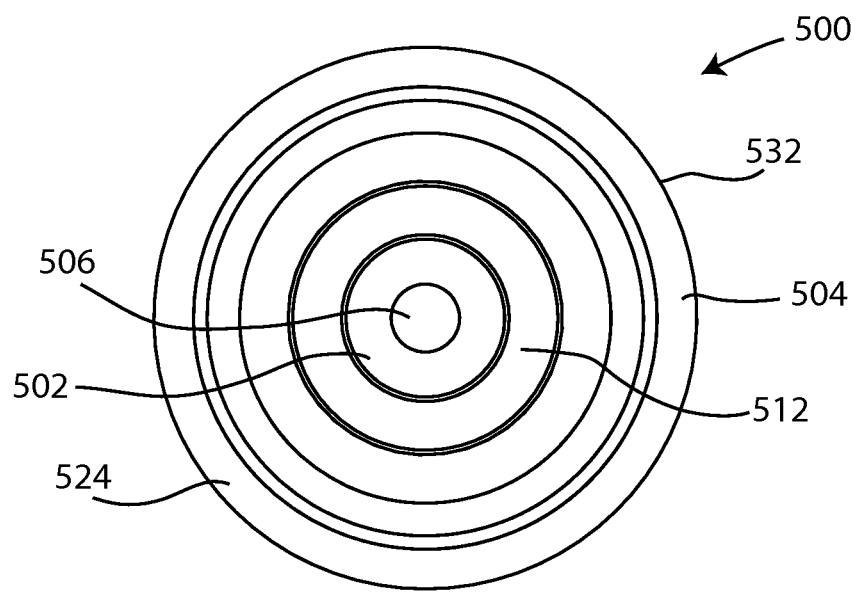
FIG. 5 is a bottom view of the radial head implant of FIG. 1.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk. In the context of a patient's radius, distal means toward the hand, proximal means toward the shoulder, and medial means toward the ulna.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

Referring to FIGS. 1-7 and 9-11, a radial head implant 500 includes a stem 502 and a head 504. In the embodiment depicted, the stem and head are separation components, but in other embodiments the implant may be formed integrally as one piece. The radial head implant 500 is radially symmetrical about a center longitudinal axis 501 shown in FIG. 7, and extends between an implant proximal end 503 and an implant distal end 505. The stem may be referred to as an anchor or anchoring portion.

The stem 502 includes a tip portion 506, a shaft portion 508, and an attachment portion 510. The tip portion 506 tapers distally, and may be described as bullet-shaped. The bullet-shape tip may provide for ease of insertion of the implant into the intramedullary canal. The shaft portion 508 extends between the tip 506 and attachment 510 portions, and is wider in diameter than the tip portion 506, and narrower in diameter than the attachment portion 510. In the embodiment shown, the shaft portion 508 is cylindrical, having a fixed diameter, and a constant radius from the center longitudinal axis 501. The attachment portion 510 is generally disc-shaped, and tapers slightly toward its proximal end.

In an embodiment, at least the shaft portion 508 and tip portion 506 may be smooth, enabling movement such as rotation and/or axial tilting within the intramedullary canal during and after implantation. This smoothness and ability for slight movement may promote better fit, including surface contact, with an ulnar component. In an embodiment, the stem 502 is non-porous.

The head 504 has a proximal, or first end 520 and a distal, or second end 522. A peripheral wall 524 extends between and connects the first and second ends 520, 522. The first end 520 includes a circular rim 526 which encircles a concave portion 528. There is a smooth transition between the rim 526 and the concave portion 528. A first bearing surface 530 is formed on the first end 520, and may bear against a distal humerus or humeral implant. A second bearing surface 532 is on the exterior or the peripheral wall 524, and may bear against a proximal ulna or ulnar implant. The peripheral wall 524 and second bearing surface 532 are annular but non-cylindrical, having no constant radius from the central longitudinal axis 501. The peripheral wall and the second bearing surface may be described as circumferential, as they encircle the head 502 between the first end 520 and the second end 522.

A proximal to distal profile 534 of the second bearing surface 532, seen for example in FIG. 1, as the sides of the head 504 between the first end 520 and the second end 522, is formed of a contiguous series of arcs, with no intervening straight portions. The proximal to distal profile is defined as the outermost profile of the head 504 between the proximal end and the distal end, as seen normal to the center longitudinal axis 501. The proximal to distal profile may also be referred to as the head outer profile. The proximal to distal profile 534 may also be described as formed of arc segments of circles. The profile 534 can be subdivided into a series of profile segments, each profile segment an arc. A first profile segment 536 extends from the proximal end 520 partially along the side of the head, and is convexly curved. A second profile segment 538 extends from the first profile segment 536 farther along the side of the head, is convexly curved, and may form a portion of a sphere centered on axis 501. A third profile segment 540 extends from the second profile segment 538 toward the distal end 522, and is concavely curved. A fourth profile segment 542 extends from the third profile segment 540 to the distal end 522, and is convexly curved. Since the head is radially symmetrical, the proximal to distal outer profile at any rotational location around the head will be the same as any other proximal to distal outer profile at any other rotational location around the head. Each profile segment has a radius of curvature.

The bearing surface 532 similarly has a first convex portion 546, a second convex portion 548, a first concave portion 550, and a third convex portion 552. Each bearing surface portion 546, 548, 550, 552 is annular about the central longitudinal axis 501. The bearing surface 532 transitions smoothly and continuously across its constituent portions. In an embodiment, the second convex portion 548 is a portion of a sphere centered on axis 501. In an embodiment, the maximum diameter of third convex portion 552 is less than the maximum diameters of the first and second convex portions 546, 548 and the first concave portion 550. In an embodiment, the maximum diameter of the first concave portion 550 is less than the maximum diameters of the first and second convex portions 546, 548. In an embodiment, the maximum diameter of the second convex portion 548 is greater than the maximum diameter of the first convex portion 546.

The convex portions 546, 548, 552 enhance clinical contact with the ulna or ulnar prosthesis, and allow flexibility in axial orientation of the stem 502. The convex portions accommodate a radius whose proximal canal axis is not parallel with the ulnar articulation surface of the ulna or ulnar prosthesis. The concave portion 550 allows easier insertion of the implant 500 into the proximal radius by reducing engagement with the distal humerus during implantation. The tapered or bullet shape of the tip portion 506 may also facilitate insertion into the proximal radius.

Figure 6:
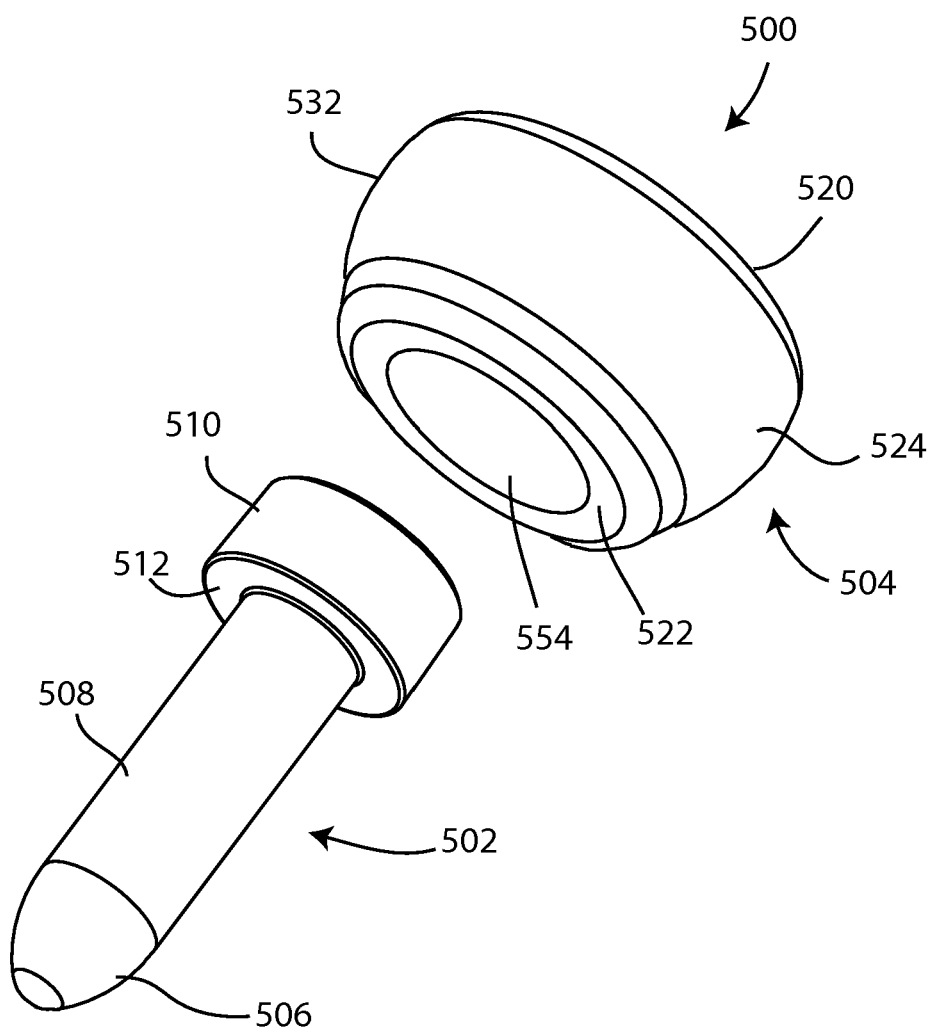
FIG. 6 is an isometric exploded view of the radial head implant of FIG. 1, with the stem and head portions separated.
Figure 7:
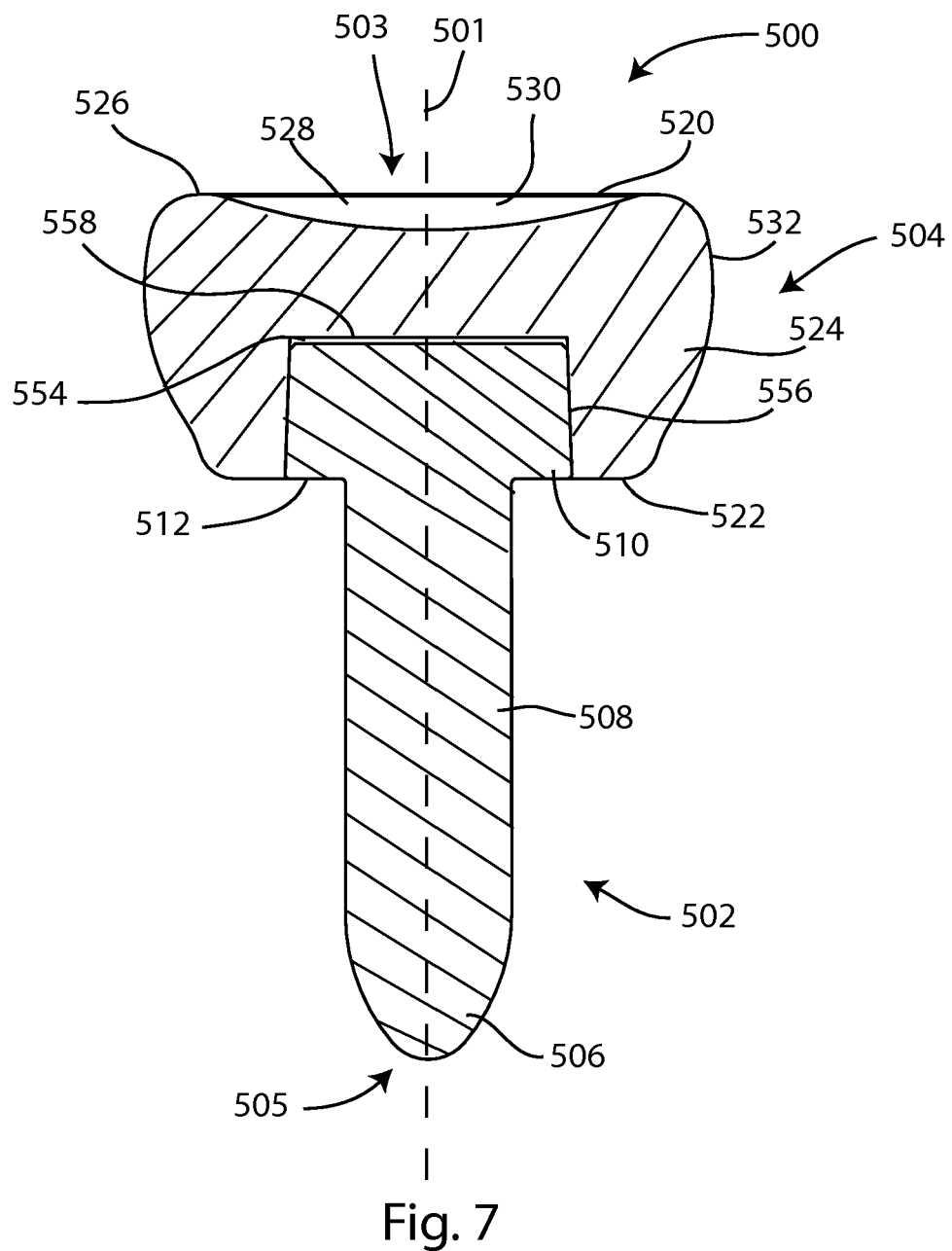
FIG. 7 is a longitudinal cross-sectional view of the radial head implant of FIG. 1 taken along line A-A of FIG. 1.

The distal end 522 of the head includes a recess 554, seen in FIGS. 6 and 7. The recess 554 is shaped as a blind bore to receive the stem attachment portion 510. The recess 554 includes an annular sidewall 556 and an endwall 558. The sidewall 556 may taper toward the endwall 558, so that a diameter of the recess at its opening at distal end 522 is greater than its diameter at endwall 558. The outer diameter of attachment portion 510 and diameter of recess 554 cooperate to enable a secure press fit between the head 504 and the stem 502. In an embodiment, the attachment portion 510 and recess 554 are tapered to provide a complementary fit between the attachment portion and the recess. When stem 502 is properly received in the recess 554 of the head 504, a distal end 512 of the attachment portion 510 is flush with the head distal end 522.

Figure 8:
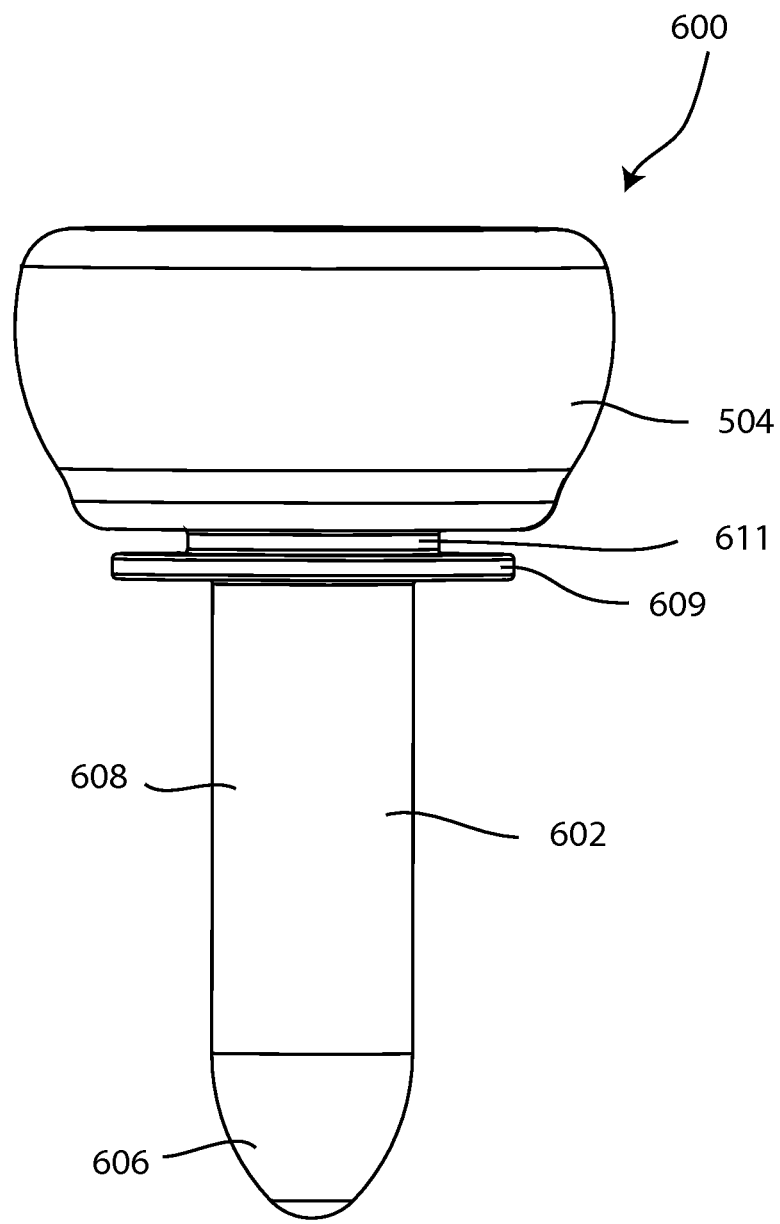
FIG. 8 is an alternative embodiment of a radial head implant having a collar offset from the head.
Figure 9:
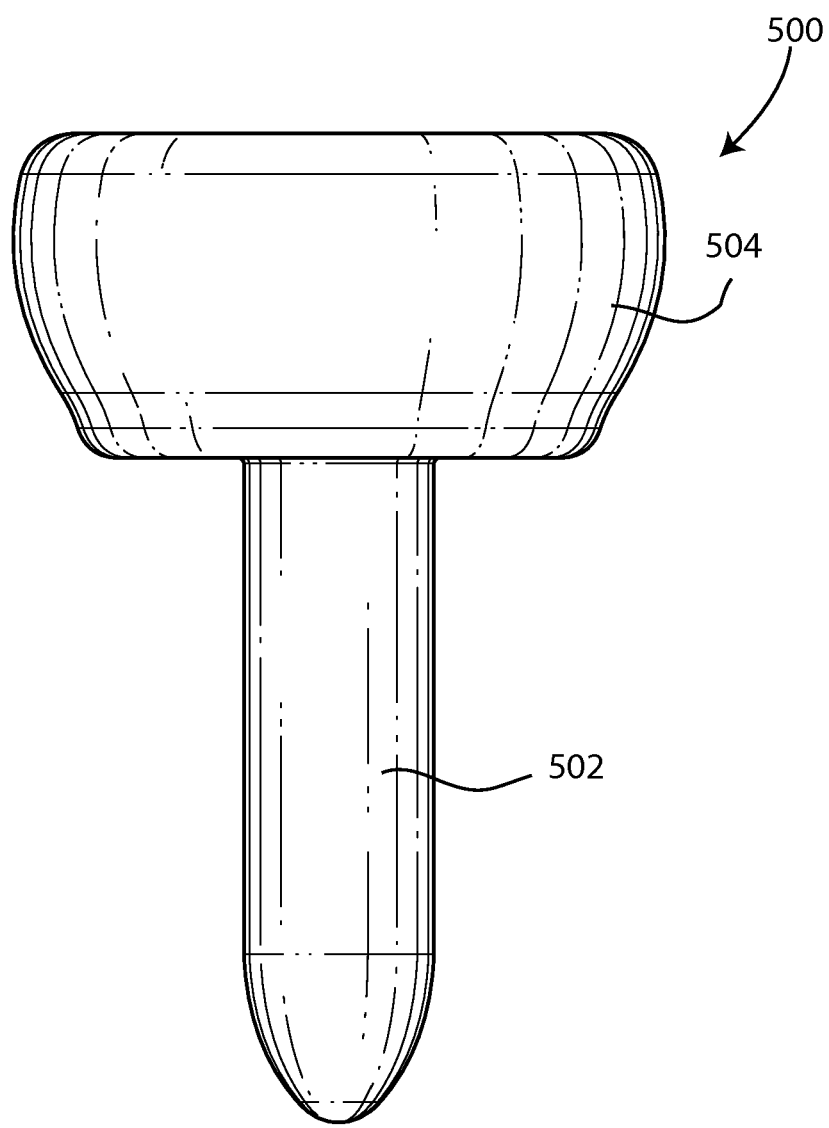
FIG. 9 is another side view of the radial head implant of FIG. 1.
Figure 10:
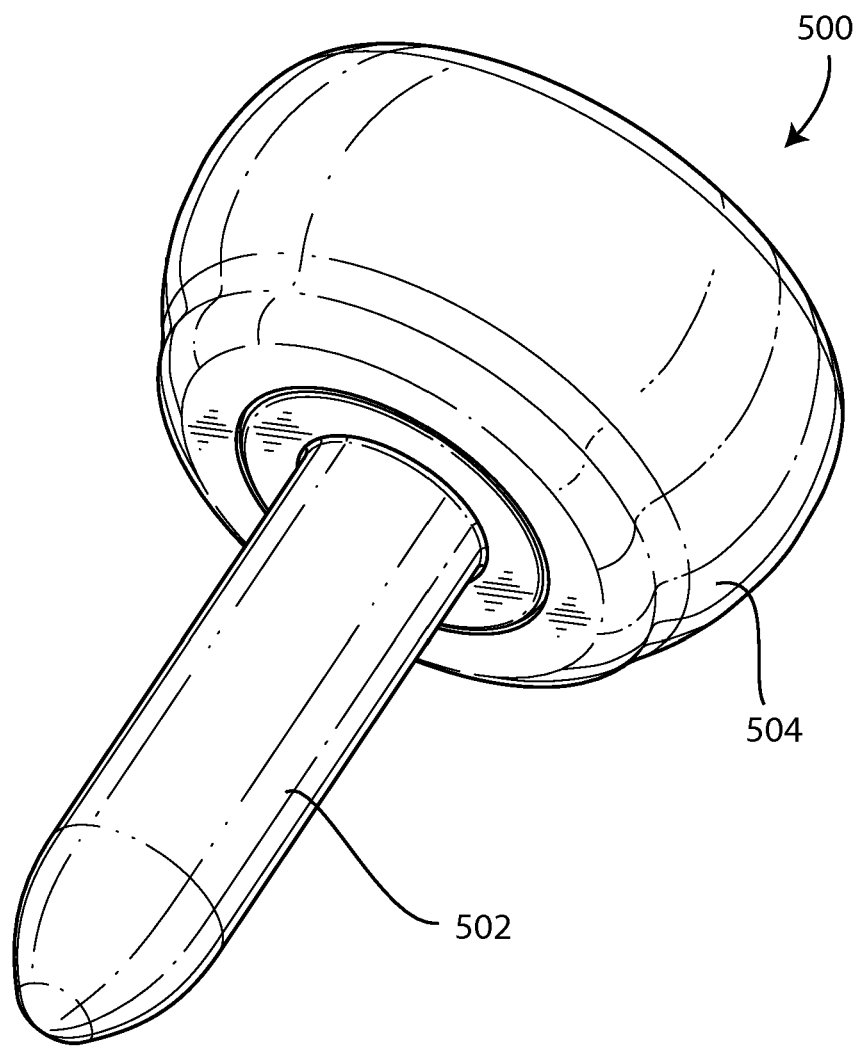
FIG. 10 is a perspective view of the radial head implant of FIG. 1.
Figure 11:
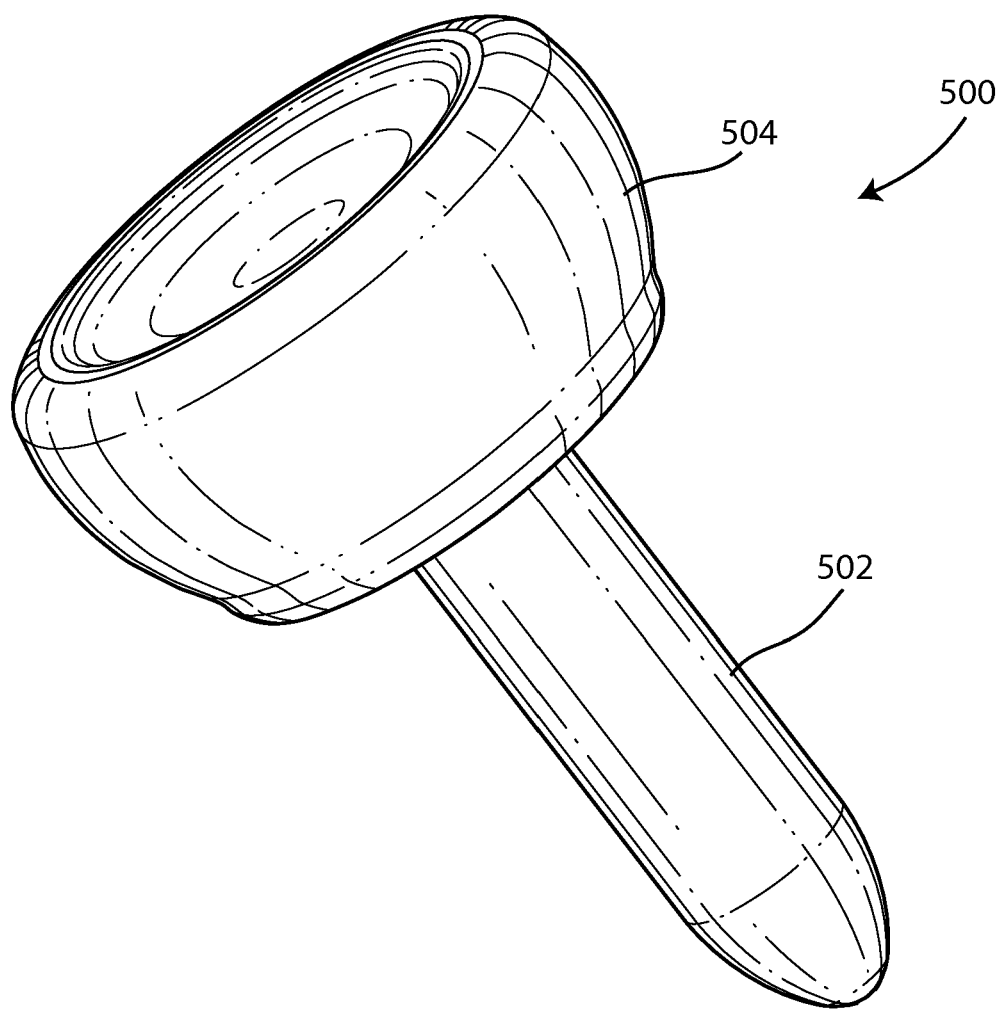
FIG. 11 is another perspective view of the radial head implant of FIG. 1.

Referring to FIG. 8, an alternative embodiment of a radial head prosthesis is shown. Radial head implant 600 includes stem 602 and head 504. Stem 602 includes a tip portion 606, a shaft portion 608, and an attachment portion. The attachment portion of the stem 602 is shown positioned within the head 504, and is therefore not visible in FIG. 8. A collar 609 encircles the stem toward the proximal end of the stem, and projects radially from the shaft portion 608. A neck portion 611 of stem is proximal to the collar 609 and distal to the attachment portion. The collar 609 may be smaller in diameter than the minimum diameter of the head 504. The neck portion 611 may be larger in diameter than the shaft portion 608. Other than the inclusion of the collar and neck portion, the description of radial head implant 500 applies to radial head implant 600. Thus, although not visible in FIG. 8, the attachment portion of the stem 602 is similar to the attachment portion 510 of the stem 502. The collar 609 can have the effect of raising the attachment of the stem to the head proximally relative to the bone resection surface.

In some embodiments, the relative widths of head peripheral wall 524, recess 554 and stem attachment portion 510 may vary. For example, in an embodiment peripheral wall 524 may be wider and recess 554 narrower, to fit on an attachment portion 510 which is equal in diameter to shaft portion 508. In another embodiment, peripheral wall 524 may be relatively narrower, and recess 554 and attachment portion 510 relatively wider.

The radial head implants 500, 600 may be available in a variety of sizes. For example, the distal to proximal length, and the diameter of the stem 502 may be varied to result in differently sized implants. The distal to proximal height, and the diameter of the head 504 may be varied to result in differently sized implants.

Some embodiments may include a stem component having a shaft that is curved, or a shaft that is multi-segmented, having 2 or more angled segments. The outer peripheral surface of the shaft may be generally rounded or cylindrical, or may be multi-faceted. In cross-section, the shaft may be circular, square, rectangular, triangular, hexagonal, star-shaped, or another cross-sectional shape. Any of the devices disclosed herein may include markings to indicate size or other characteristics.

The implant 500 may be formed of one or more metals or metal alloys, including but not limited to stainless steel, titanium, and cobalt-chrome. Some or all of the implant may be formed of polymers including acetal, polyphenylsulfone (PPSU), polyetherimide (PEI), polyether ether ketone (PEEK), polyethylene (PE) and/or orthers including high molecular weight grades. The head and stem components may comprise the same material, or different materials.

In a method of use, a patient's distal radius is prepared to receive the implant 500. The anatomic proximal radial head is resected, and a planar resection surface may be created which intersects with the intramedullary canal. A pilot passage may be created extending distally into the intramedullary canal. The stem 502 is inserted into the intramedullary canal, with tip portion 506 pointed distally. The stem 502 may be inserted until the distal end of the stem 512 contacts the resection surface. The head 504 is moved axially and mounted on the stem 502 with stem attachment portion 510 received in recess 554. In an embodiment, the head 504 is moved axially along axis 501 until recess 554 is engaged on attachment portion 510. Alternatively, the head 504 may be attached to the stem 502 prior to implantation, and the implant 500 implanted as one piece into the prepared proximal radius. Implant 600 may be implanted using the same method; however collar 609 may contact the resected bone surface.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An implantable prosthesis for replacing the proximal head of a radius, the radius distal to a humerus and adjacent an ulna, the radius having an intramedullary canal, the prosthesis comprising:

a stem portion for insertion into the intramedullary canal to anchor the prosthesis in the radius, the stem portion including a proximal end, a distal end, and a head attachment portion at the stem proximal end, the head attachment portion including an outwardly extending distal surface, wherein the head attachment portion tapers towards the stem proximal end; and a radial head portion attachable to the stem portion, the head portion having a proximal end, a distal end including a distal surface, and a circumferential peripheral wall extending between the proximal end and the distal end, wherein the head portion is radially symmetrical about a center longitudinal axis of the head portion, the head distal end including a bore that tapers proximally towards an endwall thereof and is mateable, in a complementary manner, with the tapered head attachment portion to form a press-fit connection, the head proximal end including a first bearing surface for articulation with the humerus, the circumferential peripheral wall including a second bearing surface for articulation with the ulna, the second bearing surface defining a proximal to distal profile between the proximal and distal ends of the head portion;

wherein the second bearing surface includes first and second convex portions, a first concave portion, and a third convex portion, wherein the entire proximal to distal profile of the second bearing surface is either concavely or convexly curved;

wherein the distal surface of the head attachment portion is flush with the distal surface of the head distal end when the stem portion and the head portion are in an assembled state.

2. The prosthesis of claim 1, wherein the stem portion includes a shaft portion and a tip portion, wherein the shaft portion is cylindrical.

3. The prosthesis of claim 1, wherein the head portion is attached to the stem portion by moving the head portion axially toward the stem portion.

4. The prosthesis of claim 1, wherein the second convex portion is positioned between the first convex portion and the first concave portion, and wherein each second bearing surface portion has a maximum diameter.

5. The prosthesis of claim 4, wherein the maximum diameter of the second convex portion is greater than the maximum diameters of the first convex portion and the first concave portion.

6. The prosthesis of claim 4, wherein the head portion tapers proximally to distally, wherein the first concave portion is positioned between the second convex portion and the third convex portion, wherein the maximum diameter of the second convex portion is greater than the maximum diameter of the first concave portion, and the maximum diameter of the first concave portion is greater than the maximum diameter of the third convex portion.

7. The prosthesis of claim 4, wherein the second convex portion is spherical.

8. The prosthesis of claim 1, wherein the head portion is attachable to the stem portion in a fixed configuration, the head portion being restrained from rotational movement relative to the stem portion.

9. An implantable prosthesis for replacing the proximal head of a radius, the radius distal to a humerus and adjacent an ulna, the radius having an intramedullary canal, the prosthesis comprising:
  a stem portion for insertion into the intramedullary canal to anchor the prosthesis in the radius, a proximal end of the stem portion including a tapered head attachment portion, the tapered head attachment portion including an outwardly extending distal surface; and
  a radial head portion attachable to the stem portion in a fixed configuration by insertion of the tapered head attachment portion into a complementary tapered bore in the head portion, the tapered head attachment portion and the complementary tapered bore forming a press-fit connection, whereby the head portion is restrained from rotational movement relative to the stem portion, the head portion having a proximal end, a distal end including a distal surface, and a circumferential peripheral wall extending between the proximal end and the distal end;
  wherein the head portion is radially symmetrical about a center longitudinal axis of the head portion;
  wherein the head portion has a head outer profile defined between the proximal end and the distal end, the entire head outer profile consisting of a contiguous series of arc segments, including at least one concavely curved arc segment and at least one convexly curved arc segment; and
  wherein the distal surface of the tapered head attachment portion is flush with the distal surface of the head distal end when the stem portion and the head portion are in an assembled state.

10. The prosthesis of claim 9, wherein the stem portion includes a shaft portion and a tip portion, wherein the shaft portion is cylindrical.

11. The prosthesis of claim 9, wherein the head portion is attached to the stem portion by moving the head axially toward the stem portion.

12. The prosthesis of claim 9, wherein the tapered bore is located at the head distal end.

13. The prosthesis of claim 9, wherein the contiguous series of arc segments includes a first convex segment, a second convex segment, a first concave segment, and a third convex segment.

14. The prosthesis of claim 13, wherein the second convex segment is positioned between the first convex segment and the first concave segment, and wherein the second convex segment has a greater radius of curvature than the first convex segment and the first concave segment.

15. The prosthesis of claim 13, wherein the second convex segment is spherical.

16. The prosthesis of claim 9, wherein the head outer profile tapers proximally to distally.

* * * * *